United States Patent
Colvin, Jr. et al.

(10) Patent No.: US 7,755,022 B2
(45) Date of Patent: Jul. 13, 2010

(54) SYSTEM AND METHOD FOR ATTENUATING THE EFFECT OF AMBIENT LIGHT ON AN OPTICAL SENSOR

(75) Inventors: Arthur E. Colvin, Jr., Mt. Airy, MD (US); Paul Samuel Zerwekh, Shawsville, VA (US); Jeffrey C. Lesho, Brookeville, MD (US); Robert W. Lynn, Germantowm, MD (US); Carrie R. Lorenz, Woodbine, MD (US); Casey J. O'Connor, Gaithersburg, MD (US); Steven J. Walters, Ellicott City, MD (US)

(73) Assignee: Sensors for Medicine and Science, Inc., Germantown, MD (US)

( * ) Notice: Subject to any disclaimer, the term of this patent is extended or adjusted under 35 U.S.C. 154(b) by 0 days.

(21) Appl. No.: 12/180,745

(22) Filed: Jul. 28, 2008

(65) Prior Publication Data

US 2009/0039286 A1 Feb. 12, 2009

Related U.S. Application Data

(60) Continuation of application No. 11/646,266, filed on Dec. 28, 2006, now Pat. No. 7,405,387, which is a division of application No. 10/823,781, filed on Apr. 14, 2004, now Pat. No. 7,157,723.

(60) Provisional application No. 60/462,695, filed on Apr. 15, 2003.

(51) Int. Cl.
*G01J 1/16* (2006.01)
*F21V 9/16* (2006.01)

(52) U.S. Cl. .............................. 250/214 AL; 250/458.1

(58) Field of Classification Search ............ 250/214 AL, 250/214 B, 214 C, 214 R, 458.1
See application file for complete search history.

(56) References Cited

U.S. PATENT DOCUMENTS

| | | | |
|---|---|---|---|
| 5,302,393 A | 4/1994 | Matsumoto et al. | |
| 5,672,881 A | 9/1997 | Striepeke et al. | |
| 5,720,771 A | 2/1998 | Snell | |
| 5,801,684 A * | 9/1998 | Uskali | 345/213 |
| 5,833,603 A | 11/1998 | Kovacs et al. | |
| 6,015,386 A | 1/2000 | Kensey et al. | |
| 6,201,980 B1 | 3/2001 | Darrow et al. | |
| 6,305,602 B1 * | 10/2001 | Grabowski et al. | 235/379 |
| 6,315,719 B1 | 11/2001 | Rode et al. | |
| 6,330,464 B1 | 12/2001 | Colvin, Jr. et al. | |
| 6,400,974 B1 | 6/2002 | Lesho | |
| 6,491,647 B1 * | 12/2002 | Bridger et al. | 600/585 |
| 6,682,480 B1 * | 1/2004 | Habib et al. | 600/300 |
| 6,687,515 B1 * | 2/2004 | Kosaka | 455/566 |
| 6,864,795 B2 * | 3/2005 | Smith et al. | 340/573.1 |
| 6,867,051 B1 | 3/2005 | Anderson et al. | |
| 6,911,909 B2 | 6/2005 | Chandar | |
| 6,976,626 B2 * | 12/2005 | Schmidt et al. | 235/462.01 |

(Continued)

FOREIGN PATENT DOCUMENTS

WO 0224048 A2 3/2002

*Primary Examiner*—John R Lee
(74) *Attorney, Agent, or Firm*—Rothwell, Figg, Ernst & Manbeck, pc

(57) ABSTRACT

The present invention provides systems and methods for attenuating the effect of ambient light on optical sensors and for measuring and compensating quantitatively for the ambient light.

9 Claims, 10 Drawing Sheets

U.S. PATENT DOCUMENTS

| | | | |
|---|---|---|---|
| 7,020,508 B2 * | 3/2006 | Stivoric et al. | 600/390 |
| 7,157,723 B2 * | 1/2007 | Colvin et al. | 250/458.1 |
| 7,227,156 B2 * | 6/2007 | Colvin et al. | 250/458.1 |
| 7,405,387 B2 * | 7/2008 | Colvin et al. | 250/214 AL |
| 2002/0016535 A1 | 2/2002 | Martin et al. | |
| 2002/0026108 A1 | 2/2002 | Colvin, Jr. | |
| 2003/0001738 A1 * | 1/2003 | Chandar | 340/568.1 |
| 2003/0197610 A1 * | 10/2003 | Chandar | 340/568.1 |
| 2004/0054270 A1 * | 3/2004 | Pewzner et al. | 600/341 |
| 2004/0133092 A1 * | 7/2004 | Kain | 600/377 |
| 2005/0035304 A1 * | 2/2005 | Colvin et al. | 250/458.1 |
| 2007/0102649 A1 * | 5/2007 | Colvin et al. | 250/458.1 |

* cited by examiner

SYSTEM AND METHOD FOR ATTENUATING THE EFFECT OF AMBIENT LIGHT ON AN OPTICAL SENSOR

The present application is a continuation of U.S. patent application Ser. No. 11/646,266, filed Dec. 28, 2006, which is a divisional of U.S. patent application Ser. No. 10/823,781, filed Apr. 14, 2004, now U.S. Pat. No. 7,157,723, issued Jan. 2, 2008, which claims the benefit of U.S. Provisional Patent Application No. 60/462,695, filed Apr. 15, 2003.

BACKGROUND OF THE INVENTION

1. Field of the Invention

The present invention relates to optical sensors, and, more specifically, to a system and method for attenuating the effect of ambient light on an optical sensor.

2. Discussion of the Background

An optical sensor is a device that may be used to detect the concentration of an analyte (e.g., oxygen, glucose, or other analyte). U.S. Pat. No. 6,330,464, the disclosure of which is incorporated herein by reference, describes an optical sensor.

There may be situations when it is desirable to use an optical sensor in an environment where there is a significant amount of ambient light (e.g., the outdoors on a bright, sunny day). In some circumstances, a significant amount of ambient light may negatively affect the accuracy of an optical sensor. Accordingly, what is desired are systems and methods to attenuate the negative effect of ambient light on the functioning of an optical sensor and/or to measure and compensate quantitatively for the ambient light.

SUMMARY OF THE INVENTION

The present invention provides systems and methods for attenuating the effect of ambient light on optical sensors and for measuring and compensating quantitatively for the ambient light.

In one aspect, the present invention provides an optical sensor having features that attenuate the amount of ambient light that reaches the optical sensor's photodetectors. The features can be used together or separately. For example, in some embodiments, the present invention provides an optical sensor wherein the circuit board that is used to electrically connect the electrical components of the sensor is made from an opaque material (e.g., opaque ferrite), as opposed to the conventional aluminum oxide ceramic circuit board. In some embodiments, the photodetectors of the optical sensor are mounted to the bottom side of a circuit board and holes are made in the circuit board to provide a way for light from the indicator molecules to reach the photodetectors.

In another aspect, the present invention provides methods for using and implanting an optical sensor, which methods, used together or separately, reduce the effect of ambient light on the optical sensor.

For example, in one aspect the present invention provides a method that includes the following steps: illuminating indicator molecules, thereby causing the indicator molecules to emit light; determining the amount of light reaching a photodetector at a point in time when the indicator molecules are illuminated, thereby determining the sum of the amount of ambient light and the light emitted from the indicator molecules reaching the photodetector; ceasing illuminating the indicator molecules; after ceasing illuminating the indicator molecules, determining the amount of light reaching the photodetector, thereby determining the amount of ambient light reaching the photodetector; and determining the amount of light emitted from the indicator molecules that reached the photodetector by subtracting the second determined amount of light from the first determined amount of light.

In another aspect, the present invention provides an improved sensor reader and method of operating the sensor reader. For example, in one aspect, the present invention provides a method performed by a sensor reader that includes the steps of: determining the intensity of ambient light; determining whether the intensity of the ambient light is greater than a predetermined threshold intensity; and issuing a warning to the user if it is determined that the intensity of the ambient light is greater than the predetermined threshold intensity.

The above and other features and advantages of the present invention, as well as the structure and operation of preferred embodiments of the present invention, are described in detail below with reference to the accompanying drawings.

BRIEF DESCRIPTION OF THE DRAWINGS

The accompanying drawings, which are incorporated herein and form part of the specification, help illustrate various embodiments of the present invention and, together with the description, further serve to explain the principles of the invention and to enable a person skilled in the pertinent art to make and use the invention. In the drawings, like reference numbers indicate identical or functionally similar elements. Additionally, the left-most digit(s) of a reference number identifies the drawing in which the reference number first appears.

DETAILED DESCRIPTION OF THE PREFERRED EMBODIMENT

Figure 1:
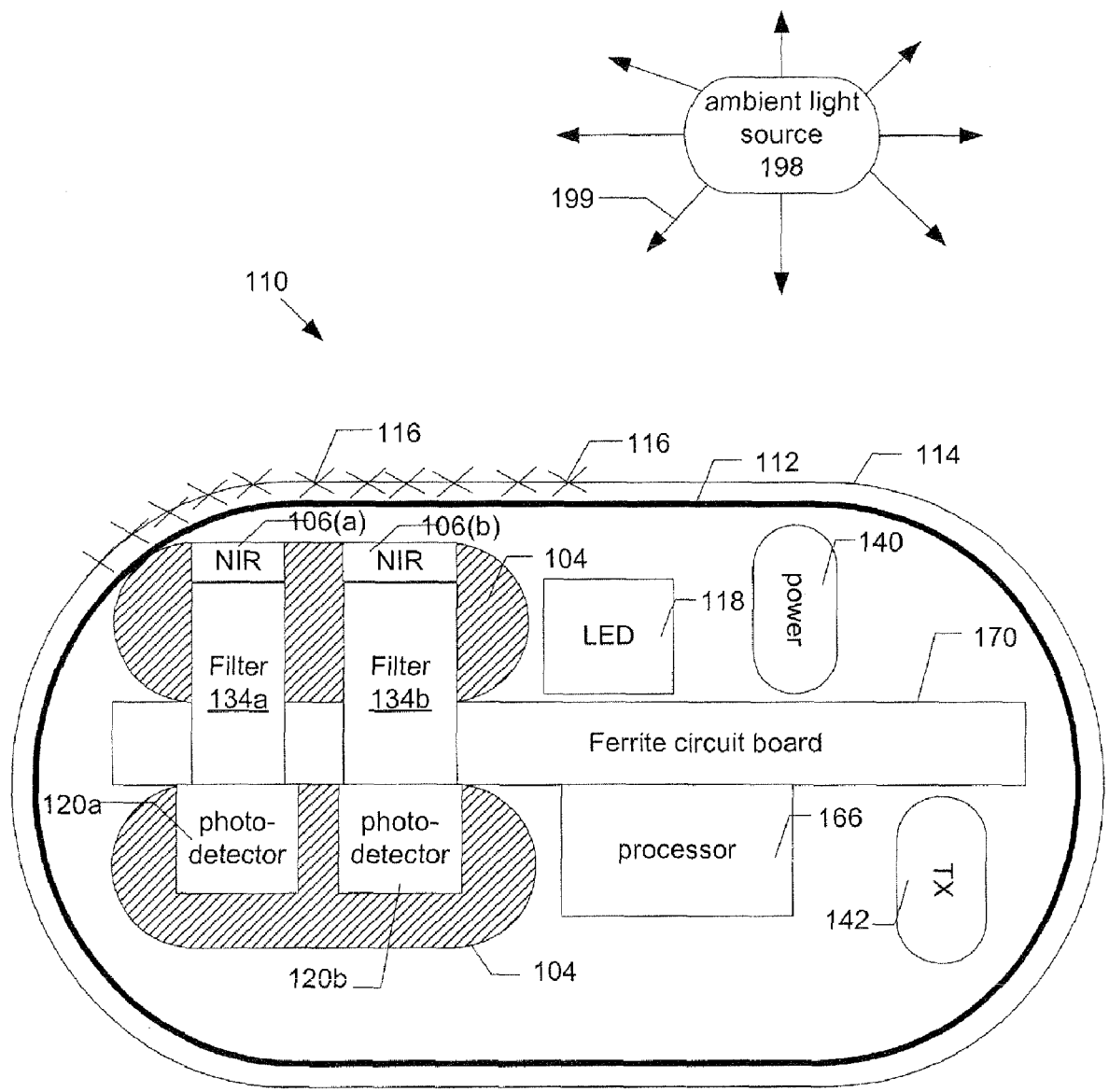
FIG. 1 shows an optical sensor according to an embodiment of the present invention.

FIG. 1 shows an optical sensor ("sensor") 110, according to an embodiment of the present invention, that operates based on the fluorescence of fluorescent indicator molecules 116. The sensor 110 includes a sensor housing 112 (sensor housing 112 may be formed from a suitable, optically transmissive polymer material), a matrix layer 114 coated over the exterior surface of the sensor housing 112, with fluorescent indicator molecules 116 distributed throughout the layer 114 (layer 114 can cover all or part of the surface of housing 112); a radiation source 118, e.g. an LED, that emits radiation, including radiation over a range of wavelengths which interact with the indicator molecules 116, i.e., in the case of a fluorescence-based sensor, a wavelength which causes the indicator molecules 116 to fluoresce; and a photodetector 120 (e.g. a photodiode, phototransistor, photoresistor or other photodetector) which, in the case of a fluorescence-based sensor, is sensitive to fluorescent light emitted by the indicator molecules 116 such that a signal is generated by the photodetector 120 in response thereto that is indicative of the level of fluorescence of the indicator molecules. Two photodetectors 120a and 120b are shown to illustrate that sensor 110 may have more than one photodetector.

The indicator molecules 116 may be coated on the surface of the sensor body or they may be contained within matrix layer 114 (as shown in FIG. 1), which comprises a biocompatible polymer matrix that is prepared according to methods known in the art and coated on the surface of the sensor housing 112. Suitable biocompatible matrix materials, which must be permeable to the analyte, include some methacrylates (e.g., HEMA) and hydrogels which, advantageously, can be made selectively permeable—particularly to the analyte—i.e., they perform a molecular weight cut-off function.

Sensor 110 may be wholly self-contained. In other words, the sensor may be constructed in such a way that no electrical leads extend into or out of the sensor housing 112 to supply power to the sensor (e.g., for driving the source 118) or to transmit signals from the sensor. Rather, the sensor may include a power source 140 that is wholly embedded or housed within the sensor housing 112 and a transmitter 142 that also is entirely embedded or housed within the sensor housing 112.

The power source 140 may be an inductor, as may be the antenna for transmitter 142 as described in U.S. Pat. No. 6,400,974. The transmitter 142 may be configured to wirelessly transmit data to an external reader (see FIG. 7).

Other self-contained power sources that can be used include microbatteries; piezoelectrics (which generate a voltage when exposed to mechanical energy such as ultrasonic sound; micro generators; acoustically (e.g., ultrasound) driven generators; and photovoltaic cells, which can be powered by light (infrared).

As shown in FIG. 1, many of the electro-optical components of sensor 112, including a processor 166, which may include electronic circuitry for controlling, among other components, source 118 and transmitter 142, are secured to a circuit board 170. Circuit board 170 provides communication paths between the components.

As further illustrated in FIG. 1, an optical filter 134, such as a high pass or band pass filter, preferably is provided on a light-sensitive surface of a photodetector 120. Filter 134 prevents or substantially reduces the amount of radiation generated by the source 118 from impinging on a photosensitive surface of the photodetector 120. At the same time, the filter allows fluorescent light emitted by fluorescent indicator molecules 116 to pass through to strike a photosensitive region of the detector 120. This significantly reduces "noise" in the photodetector signal that is attributable to incident radiation from the source 118.

However, even though filter 134 may significantly reduce "noise" created by radiation from source 118, filter 134 may not significantly attenuate "noise" from ambient light sources 198, particularly because light that passes through skin has a wavelength that may not be filtered by the filter. That is, filter 134 may not significantly prevent ambient light 199 from hitting a photosensitive surface of a photodetector 120. Accordingly, sensor 110 has other features for dealing with the ambient light.

For example, substrate 170 of sensor 110 is made of a material that does not propagate stray light or is coated with a finish that prevents it from propagating stray light. Thus, by using such a substrate 170 one can reduce the amount of ambient light reaching the photodetectors 120. In some embodiments, substrate 170 is a ferrite circuit board 170 while in other embodiments substrate 170 may be a conventional circuit board having a finish that prevents the board from propagating light.

Figure 2:
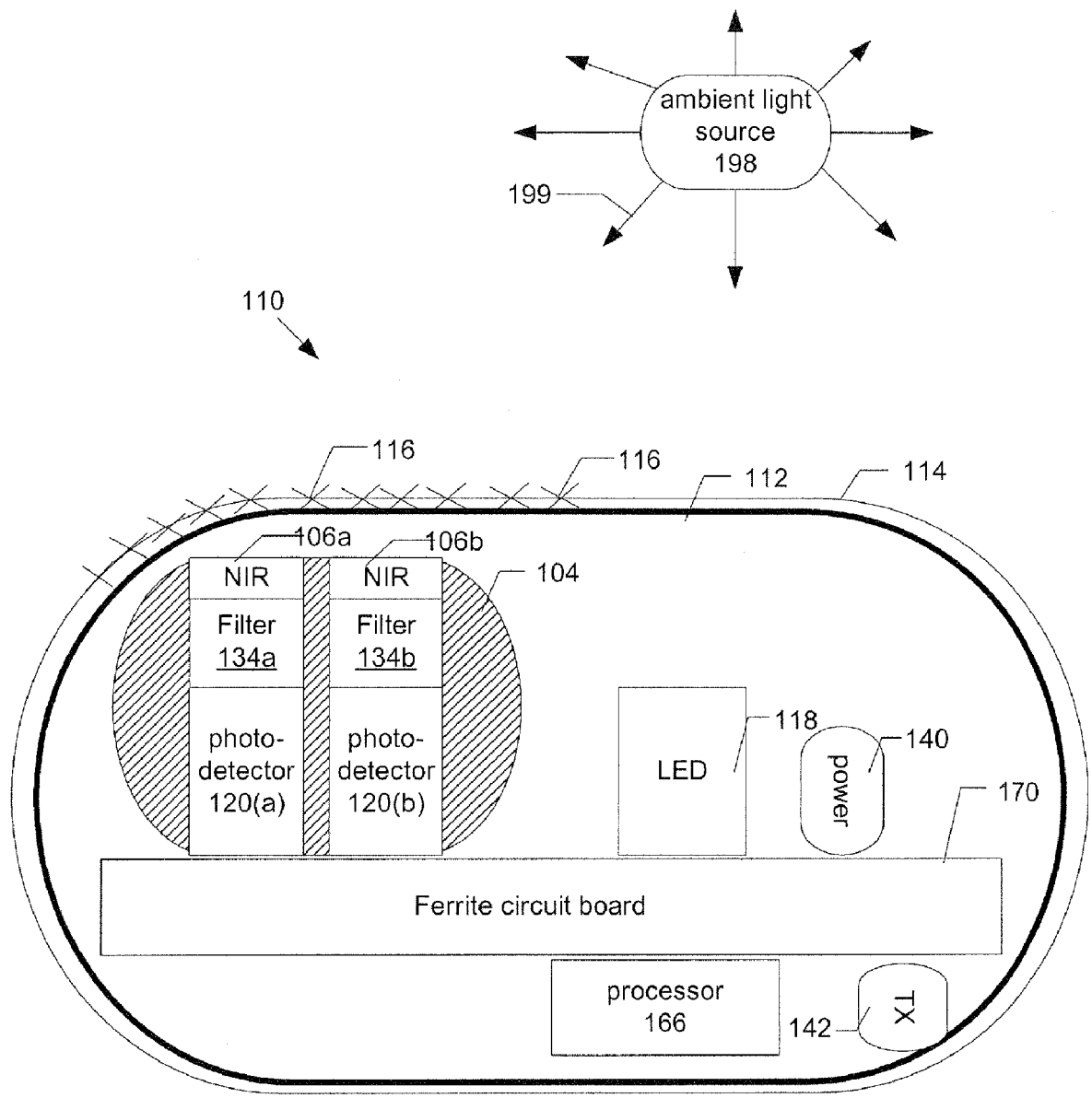
FIG. 2 shows an optical sensor according to another embodiment of the present invention.

Additionally, in sensor 110 the photodetectors 120 may be mounted to the underside of circuit board 170. This may be done by, for example, a technique known as "flip-chip" mounting. This technique of mounting the photodetectors 120 to the underside of the board 170 permits all light-sensitive surfaces except the top surface of the photodetectors 120 to be more easily covered with a light blocking substance 104 (e.g., a black, light blocking epoxy). However, it is contemplated that photodetectors 120 can be mounted on the topside of circuit board 170, as shown in FIG. 2. Like in the embodiment shown in FIG. 1, in the embodiment shown in FIG. 2 all surfaces except the top surface of the photodetector are covered with light blocking substance 104.

Figure 3:
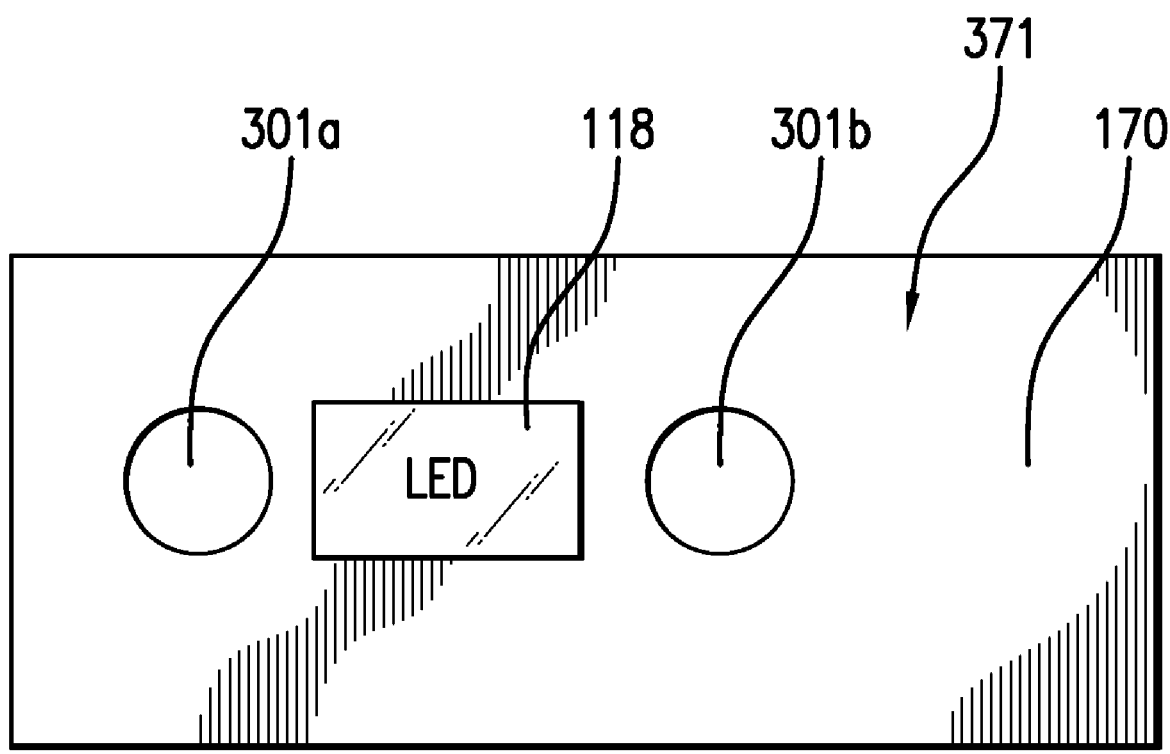
FIG. 3 shows the top surface of a circuit board according to an embodiment of the present invention.

In embodiments where the photodetectors 120 are mounted to the bottom surface of board 170, a hole for each photodetector 120 is preferably created through board 170. This is illustrated in FIG. 3, which is a top view of board 170. As shown in FIG. 3, the light source 118 is preferably mounted to the top surface 371 of board 170. As further shown in FIG. 3, two holes 301a and 301b have been created through board 170, thereby providing a passageway for light from the indicator molecules to reach the photodetectors 120. The holes in circuit board 170 may be created by, for example, drilling and the like. Preferably, each photodetector 120 is positioned such that its face is directly beneath and covering a hole, as shown in FIG. 1.

This technique restricts light from entering the photodetectors 120 except from their face and through the hole through the ferrite. As further illustrated in FIG. 1, each hole in the ferrite may be filled with an optical pass filter 134 so that light can only reach a photodetector 120 by passing through the filter 134.

As mentioned above and illustrated in FIG. 1, the bottom surface and all sides of the photodetectors 120 may be covered with black light blocking epoxy 104. Additionally, to minimize unwanted reflections that might occur from parts on the top surface 371 of the circuit board 170, a black epoxy may be used as a potting for all components not within the far-field pattern of the optical system. Further, black epoxy may be used to encircle the filters 134 for each photodetector 120, thereby preventing light leakage from propagating through a glue joint created by the mechanical tolerance between the filters 134 and circuit board holes 301.

As further shown in FIG. 1, NIR filters 106a and 106b may be positioned on top of filters 134a and 134b, respectively. Such a configuration would require all light reaching a photodetector 120 to pass through not only filter 134, but also NIR filter 106.

As FIGS. 1 and 2 make clear, any ambient light that reaches a photodetector 120 must first pass through the matrix 114 containing the indicator molecules and the filters before the light can strike the top surface of the photodetector 120 and, thereby interfere with the optical sensor. Although the matrix 114 is characteristically clear, by increasing the water content of the polymerization reaction, a phase separation occurs which results in a highly porous matrix material 114. The large size of the pores, along with the differential refractive index of the matrix 114 (versus the surrounding medium), cause substantial light scattering within the matrix 114. This scatter is beneficial in helping to attenuate any ambient light arriving from an external source before it can enter the sensor housing. Accordingly, in some embodiments of the invention, the process of making the matrix 114 is altered so that the matrix 114 will be highly porous.

For example, in some embodiments, matrix 114 is produced by (a) combining 400 mLs HEMA with 600 mLs distilled water (a 40:60 ratio), (b) swirling to mix, (c) adding 50 uL 10% ammonium persulfate (APS) (aqueous solution) and 10 uL 50% TEMED (aqueous solution), and (d) polymerizing at room temperature 30 minutes to one hour. This process will produce a highly porous matrix (or "white gel" matrix). Polymerization at higher or lower temperatures can also be used to form a white gel matrix. An example is the formation of a 30:70 gel using 175 uL distilled water+75 uL HEMA+8.44 uL VA-044 (2,2'-Azobis[2-(2-imidazolin-2-yl) propane]dihydrochloride) (other free radical initiators such as AIBN (2,2'-Azobisisobutyronitrile) might also be used).

Another feature of sensor 110 is that at least part of the housing 112 may be doped with organic or inorganic dopants that will cause the doped part of the housing 112 to function as an optical filter. For example, it is contemplated to dope a part of housing 112 with savinyl black, which is an organic light blocking material. If necessary, under certain propagation vectors of ambient light, it is possible to selectively dope the housing 112 in such a way so as to only permit the region directly within the photodetectors' 120 field of view to propagate light. This mechanism would use a "saddle" graft architecture fabricated by the pre-machined encasement procedure.

Figure 4:
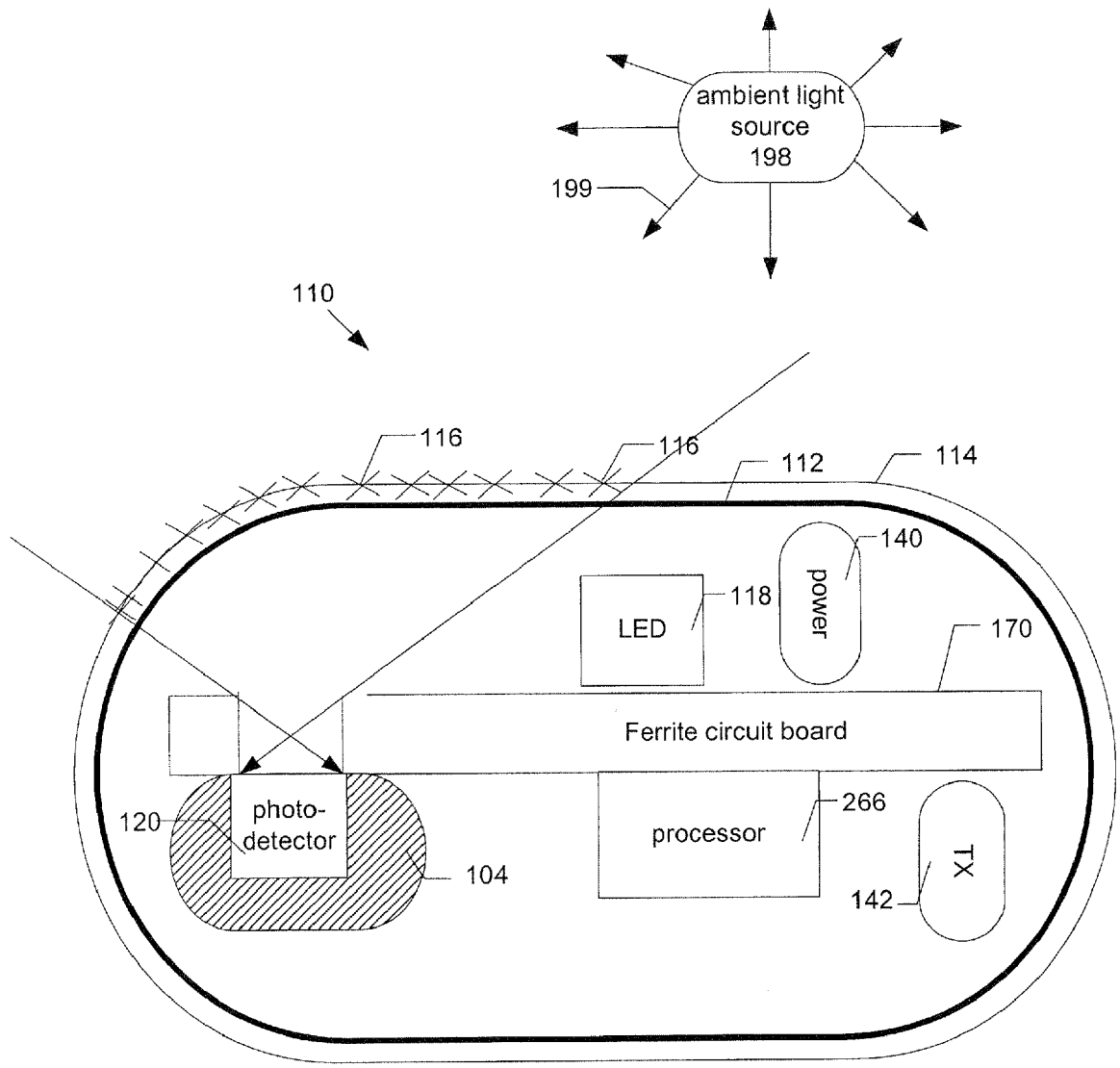
FIG. 4 shows the field of view of a photodetector according to an embodiment of the present invention.

By use of the non-transparent material 104 and the non-light propagating circuit board 170, the optical field of view of the photodetectors 120 is controlled and restricted to the region of the indicator matrix installation on the surface of the sensor housing 112. The optical field of view for one photodetector 120(a) of the embodiment shown in FIG. 1 is illustrated in FIG. 4.

Figure 5:
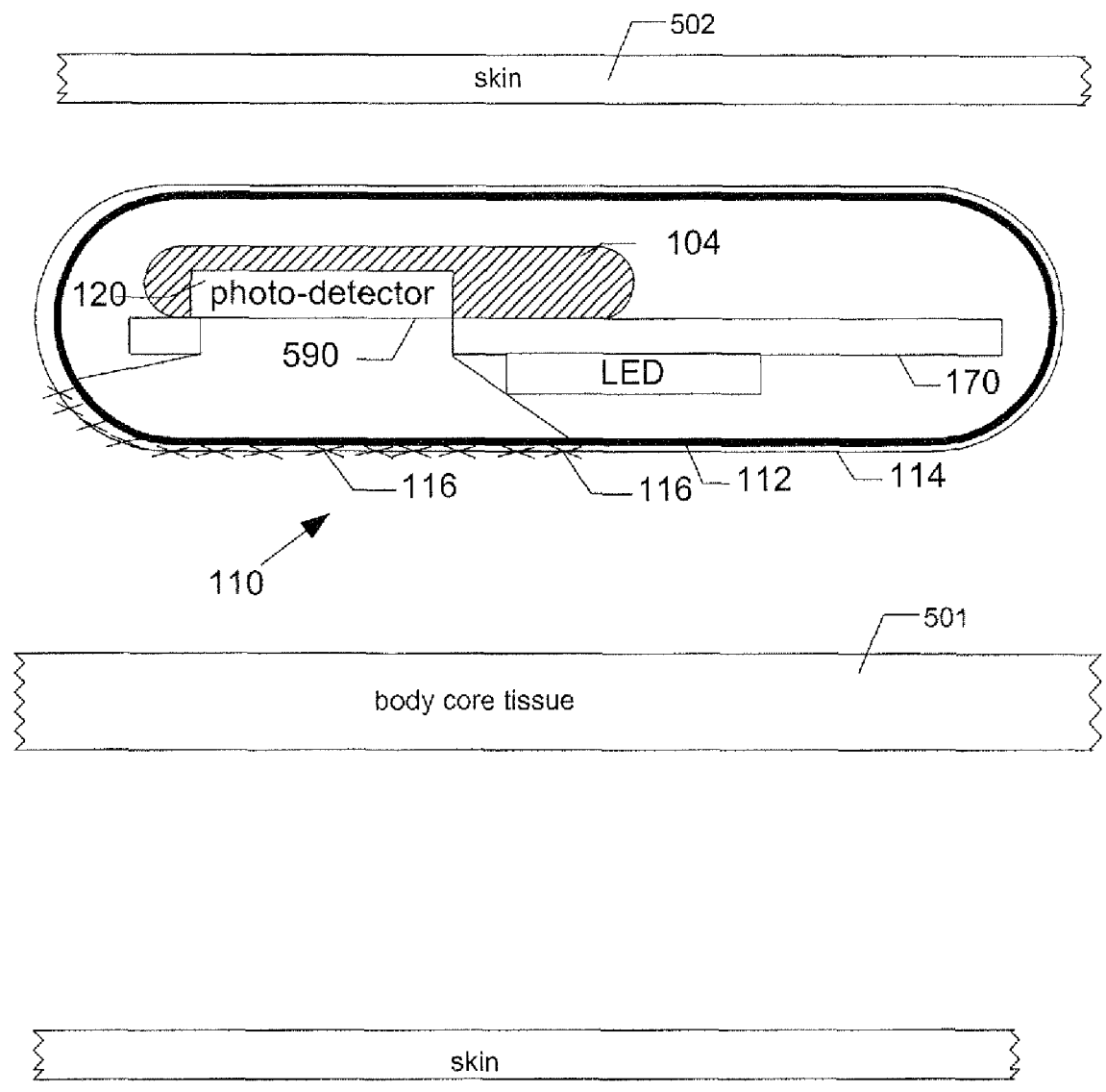
FIG. 5 shows a sensor that has been implanted into a patient according to an embodiment of the present invention.
Figure 6:
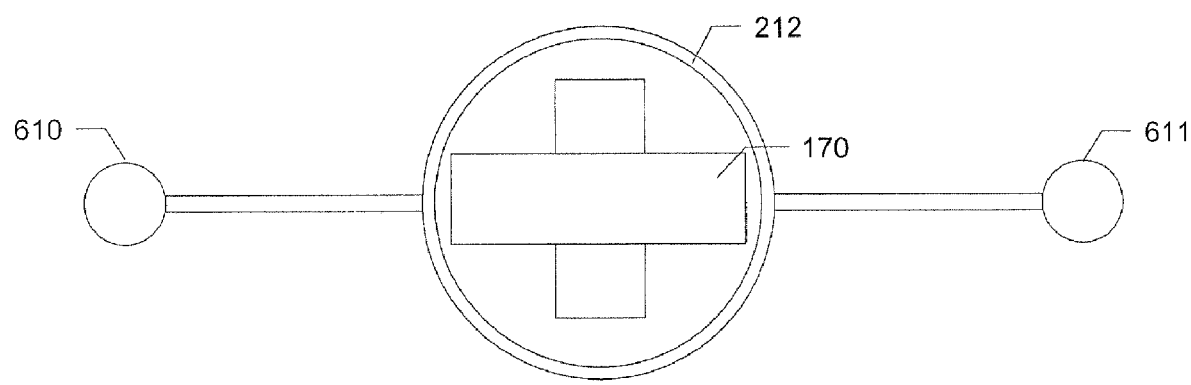
FIG. 6 shows a sensor having outriggers according to an embodiment of the present invention.

Because light cannot pass through the circuitry from the backside, the sensor 110 can be surgically installed in-vivo so as to orient the optical view of the photodetectors 120 in the most favorable placement to minimize light passing through the skin. For example, in some embodiments, orienting the sensor optical field of view inward toward body core tissue may be most favorable. This is illustrated in FIG. 5. As shown in FIG. 5, the one surface of the photodetector not covered by the non-transparent material 104 (i.e., surface 590) faces inward toward body core tissue 501 and away from the skin 520 to which it is the closest. Because it is possible that this orientation may not be maintained in-vivo following installation (e.g., the sensor might roll during normal limb movement), it is contemplated that in some embodiments it will be advantageous to incorporate anti-roll "outriggers" on the sensor housing 212. FIG. 6 is a front view of sensor 110 with outriggers 610 and 611 attached to sensor housing 212 to prevent rolling.

In addition to providing an improved optical sensor design that significantly attenuates the effect of ambient light on the proper functioning of the optical sensor 110, the present invention also provides improvements to the external signal reader that receives the output data transmitted from the optical sensor 110. As discussed above, this output data, which carries information concerning the concentration of the analyte in question, may be transmitted wirelessly from sensor 110.

Figure 7:
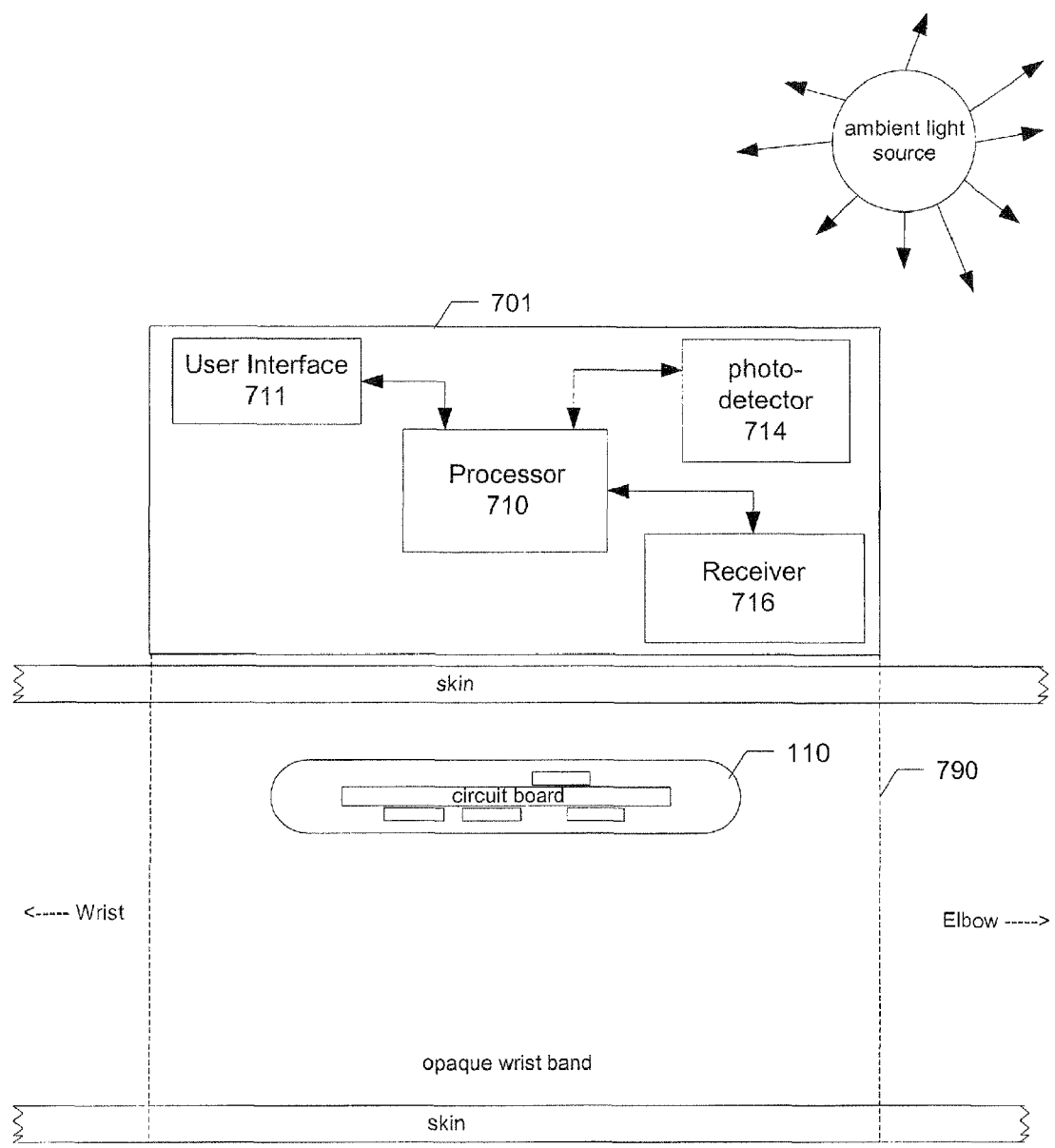
FIG. 7 shows a functional block diagram of a sensor reader according to an embodiment of the present invention.

FIG. 7 illustrates an example of an external reader 701. In the embodiment shown in FIG. 7, the optical sensor 110 is implanted near a patient's wrist and the reader 701 is worn like a watch on the patients arm. That is, reader 701 is attached to a wrist band 790. In some embodiments, reader 701 may be combined with a conventional watch. Preferably, wrist band 790 is an opaque wrist band. By wearing an opaque wrist band 790, the patient will reduce the amount of ambient light reaching the optical sensor.

As shown in FIG. 7, reader 701 includes a receiver 716, a processor 710, and a user interface 711. The user interface 711 may include a display, such as, for example, a liquid crystal display (LCD) or other type of display. The receiver 716 receives data transmitted from the sensor. The processor 710 may process the received data to produce output data (e.g., a numeric value) that represents the concentration of the analyte being monitored by the sensor.

For example, in some embodiments, sensor 110 may transmit two sets of data to reader 701. The first set of data may correspond to the output of the photodetectors 120 when the light source 118 is on and the second set of data may correspond to the output of the photodetectors 120 when the light source 118 is off.

Processor 710 processes these two data sets to produce output data that can be used to determine the concentration of the analyte being monitored by the sensor. For instance, the first set of data may be processed to produce a first result corresponding to the sum of (1) the total amount of light from the indicator molecules that reached the photodetectors 120 and (2) the total amount of ambient light that reached the photodetectors 120. The second set of data may be processed to produce a second result corresponding to the total amount of ambient light that reached the photodetectors 120. The processor 710 may then subtract the second result from the first result, thereby obtaining a final result that corresponds to the total amount of light from the indicator molecules that reached the photodetectors 120. The processor 710 may then use the final result to calculate the concentration of the analyte and cause the user interface 711 to display a value representing the concentration so that the patient can read it.

Advantageously, reader 701 may include a small photodetector 714. By including photodetector 714 in the reader 701, the reader may monitor the amount of ambient light. Further, the processor can be programmed to output a warning to the patient if the amount of ambient light detected by photodetector 714 is above a pre-determined threshold. For example, if the output of photodetector 714, which may be input into processor 710, indicates that there is a relatively high amount of ambient light, processor 710 may display an alert message on user interface 711 to alert the patient that the sensor may be non-functional due to the high amount of ambient light. The patient can then take the appropriate action. For example, the patient can move to an area where there is less ambient light or shroud the sensor so that less ambient light will reach the sensor.

Figure 8:
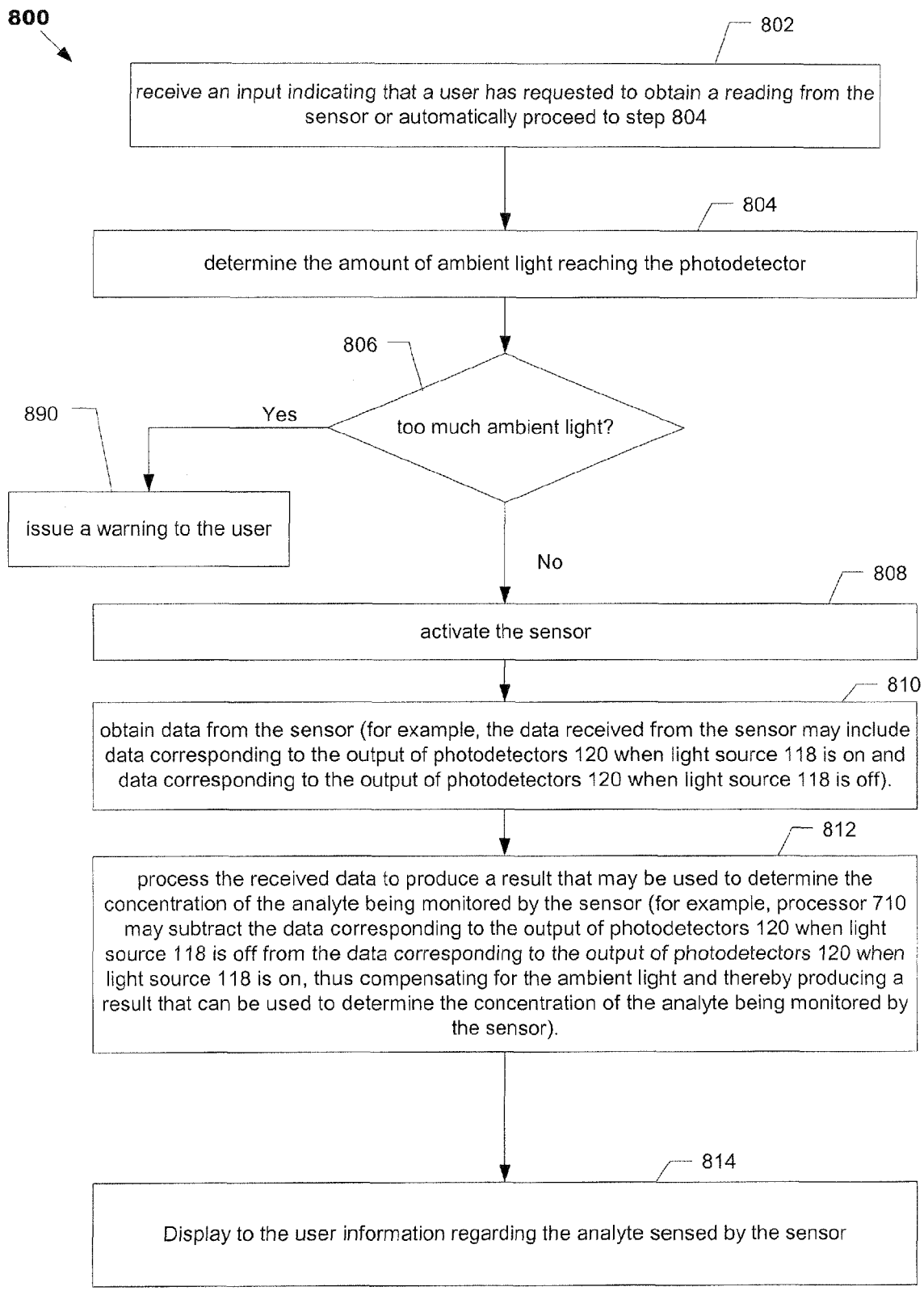
FIG. 8 is a flow chart illustrating a process, according to an embodiment of the present invention, that may be performed by a sensor reader.

FIG. 8 is a flow chart illustrating a process 800 that may be performed by processor 710. Process 800 may begin in step 802, where processor 710 receives an input indicating that a user of reader 701 has requested to obtain a reading from the sensor or where processor 710 automatically determines that it is time to obtain data from the sensor.

In step 804, processor 710 obtains from photodetector 714 information regarding the intensity of the ambient light. In step 806, processor 710 determines, based on the information obtained in step 804, whether the intensity of the ambient light is such that it is likely the sensor will not be able to function properly. For example, processor 710 may determine whether the intensity of the ambient light is greater than some pre-determined threshold. If the intensity of the ambient light is such that it is likely the sensor will not be able to function properly, then processor 710 proceeds to step 890, otherwise processor 710 proceeds to step 808.

In step 890, processor 710 issues a warning to the user. For example, processor 710 may display a message on user interface 711 or communicate to the user that there is too much ambient light.

In step 808, processor 710 activates the sensor. For example, processor 710 may wirelessly provide power to the sensor, send an activation signal to the sensor, or otherwise activate the sensor.

In step 810, processor 710 obtains data from the sensor. For example, as discussed above, the data received from the sensor may include data corresponding to the output of photodetectors 120 when light source 118 is on and data corresponding to the output of photodetectors 120 when light source 118 is off. Sensor 110 may wirelessly transmit the data to receiver 716, which then provides the data to processor 710.

In step 812, processor 710 processes the received data to produce a result that, if sensor is operating correctly (e.g., there is not too much ambient light), can be used to calculate the concentration of the analyte being monitored by the sensor. For example, as discussed above, processor 710 may subtract the data corresponding to the output of photodetectors 120 when light source 118 is off from the data corresponding to the output of photodetectors 120 when light source 118 is on to produce a result that can be used to determine the concentration of the analyte being monitored by the sensor.

In step 814, processor 710 causes information or a message regarding the analyte being sensed by the sensor to be displayed to the user, wherein the information or message is based on the result produced in step 812.

Figure 9:
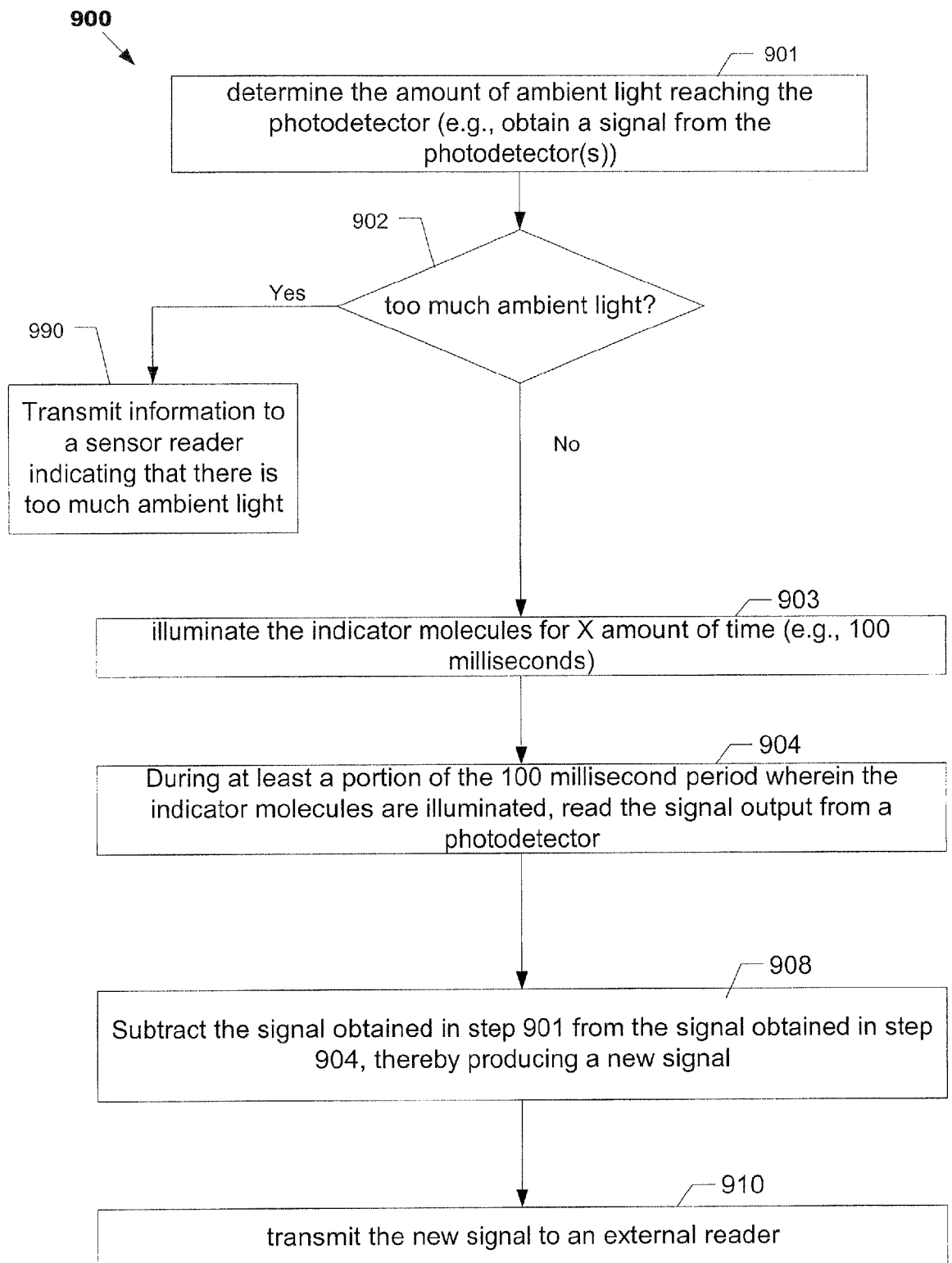
FIG. 9 is a flow chart illustrating a process for attenuating the effect of ambient light on readings provided by an optical sensor.

In addition to providing an improved optical sensor design and an improved reader, the present invention provides an improved method for operating an optical sensor, which method also attenuates the negative effect of ambient light. The method may be used with a conventional optical sensor or with optical sensors according to the present invention. FIG. 9 is a flow chart illustrating a process 900 for attenuating the effect of ambient light on readings provided by an optical sensor.

Process 900 may begin in step 901, where a determination of the amount of ambient light reaching the photodetector is made. For example, in step 901 a signal produced by one or more photodetectors is obtained during a period of time when the indicator molecules are not in a fluorescent state. In step 902, a determination is made as to whether the amount of ambient light reaching the photodetector is such that it is likely the sensor will not be able to provide an accurate reading. If the amount of ambient light reaching the photodetector is such that it is likely the sensor will not be able to provide an accurate reading, then the process proceeds to step 990, otherwise the process proceeds to step 903.

In step 990, information indicating that there is too much ambient light is transmitted to a sensor reader. After step 990, the process may end or proceed back to step 902.

In step 903, the indicator molecules are illuminated for about x amount of time (e.g., 50 or 100 milliseconds). For example, in step 903, the light source 118 may be activated for 100 milliseconds to illuminate the indicator molecules. In one embodiment, the light source is activated using about a 2 milliamp drive current. Next, while the indicator molecules are illuminated, the signal produced by a photodetector 120 is read (step 904).

Next (step 908), the signal obtained in step 901 is subtracted from the signal obtained in step 904 to produce a new signal, which new signal should better correspond to the concentration of the analyte than the signal read in step 904 because the signal read in step 904 includes not only the light emitted by the indicator molecules but also the ambient light that has reached the photodetector. Next (step 910), the new signal is transmitted to an external reader. After step 910, the process may proceed back to step 901.

Process 900 may be performed by processor 266. That is, in some embodiments, processor 266 may have software, hardware or a combination of both for performing one or more steps of process 900. For example, processor 266 may include an application specific integrated circuit (ASIC) that is designed to carry out one or more of the steps of process 900.

Figure 10:
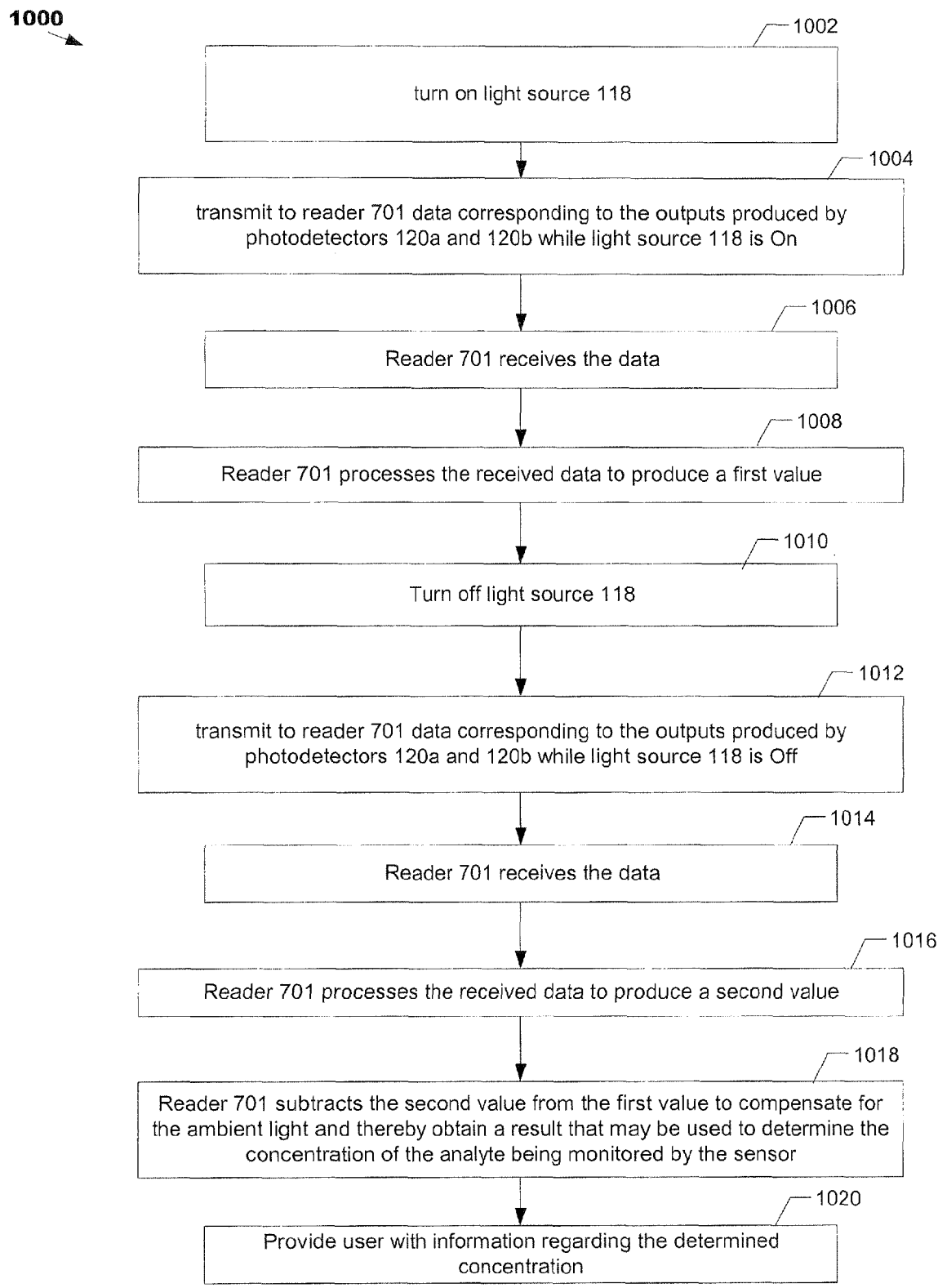
FIG. 10 is a flow chart illustrating a process performed by a sensor according to an embodiment of the invention.

FIG. 10 is a flow chart illustrating another process 1000 according to an embodiment of the invention. Process 1000 may begin in step 1002 where light source 118 is turned on for about x amount of time (e.g., 50 or 100 milliseconds). For example, in step 1002, the light source 118 may be activated for 100 milliseconds to illuminate the indicator molecules.

In step 1004, data corresponding to the outputs produced by photodetectors 120a and 120b while light source 118 is on is transmitted to reader 701. In step 1006, reader 701 receives the data. The data may include a reading from photodetector 120a and a reading from photodetector 120b, which is referred to as the reference photodetector. In step 1008, reader 701 processes the received data to produce a first value. For example, the value may be produced by dividing the reading from photodetector 120a by the reading from photodetector 120b.

Next, light source 118 is turned off (step 1010). In step 1012, data corresponding to the outputs produced by photodetectors 120a and 120b while light source 118 is off is transmitted to reader 701. In step 1014, reader 701 receives the data. The data may include a reading from photodetector 120a and a reading from photodetector 120b.

In step 1016, reader 701 processes the received data to produce a second value. For example, the second value may be produced by dividing the reading from photodetector 120a by the reading from photodetector 120b. In step 1018, reader 701 subtracts the second value from the first value to obtain a result that can be used to determine the concentration of the analyte being monitored by the sensor. In step 1020, reader 701 displays information concerning the concentration of the analyte (e.g., it displays a value representing the determined concentration).

Although the above described processes are illustrated as a sequence of steps, it should be understood by one skilled in the art that at least some of the steps need not be performed in the order shown, and, furthermore, some steps may be omitted and additional steps added.

While various embodiments/variations of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A sensor system, comprising:
an optical sensor that includes indicator molecules, a first photodetector, a light source for illuminating the indicator molecules, said photodetector configured to capture a first signal corresponding to the amount of light reaching the first photodetector at a point in time when the indicator molecules are illuminated by the light source, and said photodetector configured to also generate a second signal corresponding to the amount of light reaching the first photodetector at a point in time when the indicator molecules are not being illuminated by the light source, and a transmitter configured to transmit a wireless signal;

a sensor reader comprising a receiver for receiving said wireless signal transmitted from said sensor, a user interface for displaying information to a user of the sensor reader, and a second photodetector for detecting the intensity of ambient light; and a processor in communication with said sensor reader, said processor being configured to receive data from said second photodetector and programmed to issue an alert to a user if the data from said second photodetector indicates that the intensity of said ambient light is greater than a pre-determined threshold.

2. The sensor system according to claim 1, wherein said optical sensor is configured to generate a third signal, which is a function of said first and second signals.

3. The sensor system according to claim 2, wherein said third signal is generated by subtracting said second signal from said first signal.

4. The sensor system according to claim 2, wherein said wireless signal includes said third signal.

5. The sensor system according to claim 1, wherein the sensor reader further comprises a housing which is configured to house the receiver, user interface, and photodetector.

6. The sensor system according to claim 1, further comprising an opaque wrist band, wherein the housing is attached to the opaque wrist band.

7. The sensor system according to claim 3, wherein said photodetector data includes said ambient light signal.

8. The sensor system according to claim 1, wherein the light source is configured to be driven with about 2 milliamps of current.

9. The sensor system according to claim 1, wherein the processor is further programmed to (a) receive data transmitted from the optical sensor, (b) compute a value that is based on the data transmitted from the sensor, and (c) display the value on the user interface.

* * * * *